(12) United States Patent
Whitehurst et al.

(10) Patent No.: US 7,776,029 B2
(45) Date of Patent: Aug. 17, 2010

(54) MICROMINIATURE INFUSION PUMP

(75) Inventors: Todd K Whitehurst, Sherman Oaks, CA (US); Kelly H McClure, Simi Valley, CA (US); James P McGivern, Stevenson Ranch, CA (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 611 days.

(21) Appl. No.: 10/057,144

(22) Filed: Jan. 24, 2002

(65) Prior Publication Data

US 2004/0082908 A1    Apr. 29, 2004

Related U.S. Application Data

(60) Provisional application No. 60/265,419, filed on Jan. 30, 2001.

(51) Int. Cl.
*A61K 9/22* (2006.01)
(52) U.S. Cl. .................................... 604/890.1
(58) Field of Classification Search ............. 604/20–22, 604/890.1–892.1, 65–67, 288.01–288.04
See application file for complete search history.

(56) References Cited

U.S. PATENT DOCUMENTS

| | | | |
|---|---|---|---|
| 3,731,681 A | 5/1973 | Blackshear et al. | |
| 4,221,219 A | 9/1980 | Tucker | |
| 4,299,220 A | 11/1981 | Dorman | |
| 4,360,019 A | 11/1982 | Portner et al. | |
| 4,457,752 A | 7/1984 | Vadasz | |
| 4,482,346 A | 11/1984 | Reinicke | |
| 4,486,190 A | 12/1984 | Reinicke | |
| 4,557,673 A | 12/1985 | Chen et al. | |
| 4,772,263 A | 9/1988 | Dorman et al. | |
| 4,911,616 A | 3/1990 | Laumann, Jr. | |
| 5,041,107 A | 8/1991 | Heil, Jr. | |
| 5,045,064 A | 9/1991 | Idriss | |
| 5,049,141 A | 9/1991 | Olive | |
| 5,061,242 A | 10/1991 | Sampson | |
| 5,374,285 A * | 12/1994 | Vaiani et al. | 607/117 |
| 5,382,236 A | 1/1995 | Otto et al. | |
| 5,514,103 A | 5/1996 | Srisathapat et al. | |
| 5,578,077 A | 11/1996 | Kassatly | |
| 5,637,095 A | 6/1997 | Mason et al. | |
| 5,697,951 A | 12/1997 | Harpstead et al. | |
| 5,704,908 A * | 1/1998 | Hofmann et al. | 604/21 |
| 5,722,957 A | 3/1998 | Steinbach | |

(Continued)

OTHER PUBLICATIONS

"DUROS implant technology", printed May 14, 2001, pp. 1-2.

(Continued)

*Primary Examiner*—Nicholas D Lucchesi
*Assistant Examiner*—Christopher D Koharski
(74) *Attorney, Agent, or Firm*—Henricks, Slavin & Holmes LLP

(57) ABSTRACT

An implantable microminiature infusion device includes a reservoir for holding a therapeutic fluid or other substance and a driver, e.g., a pump, that delivers the therapeutic fluid or substance to a patient within whom the device is implanted. The device further includes at least two electrodes coupled to pulse generation circuitry, thereby allowing therapeutic electrical stimulation to also be delivered to the patient.

5 Claims, 4 Drawing Sheets

U.S. PATENT DOCUMENTS

| | | | |
|---|---|---|---|
| 5,728,396 | A | 3/1998 | Peery et al. |
| 5,733,259 | A | 3/1998 | Valcke et al. |
| 5,785,681 | A | 7/1998 | Indravudh |
| 5,814,019 | A | 9/1998 | Steinbach et al. |
| 5,820,589 | A | 10/1998 | Torgerson et al. |
| 5,836,915 | A | 11/1998 | Steinbach et al. |
| 5,888,530 | A | 3/1999 | Netti et al. |
| 5,957,890 | A | 9/1999 | Mann et al. |
| 6,048,328 | A | 4/2000 | Haller et al. |
| 6,148,222 | A * | 11/2000 | Ramsey, III ............. 600/380 |
| 6,238,367 | B1 | 5/2001 | Christiansen et al. |
| 6,283,951 | B1 * | 9/2001 | Flaherty et al. ............. 604/529 |
| 6,464,687 | B1 | 10/2002 | Ishikawa et al. |
| 6,485,464 | B1 | 11/2002 | Christenson et al. |
| 2001/0053887 | A1 | 12/2001 | Douglas et al. |
| 2002/0087147 | A1 | 7/2002 | Hooper et al. |

OTHER PUBLICATIONS

"DUROS technology: how does it work?", printed May 14, 2001, pp. 1-2.

"DUROS", printed May 14, 2001, pp. 1-2.

* cited by examiner

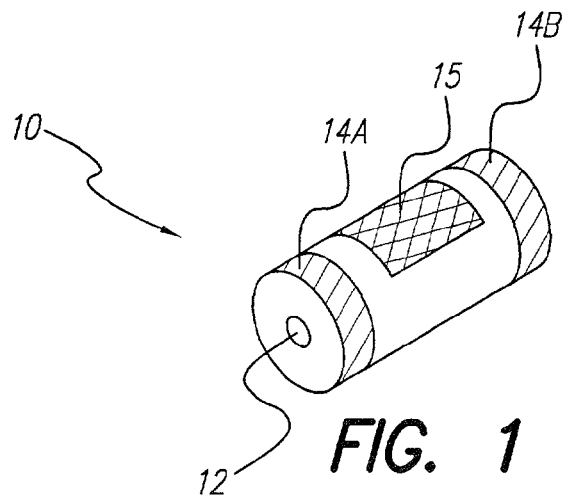
FIG. 1
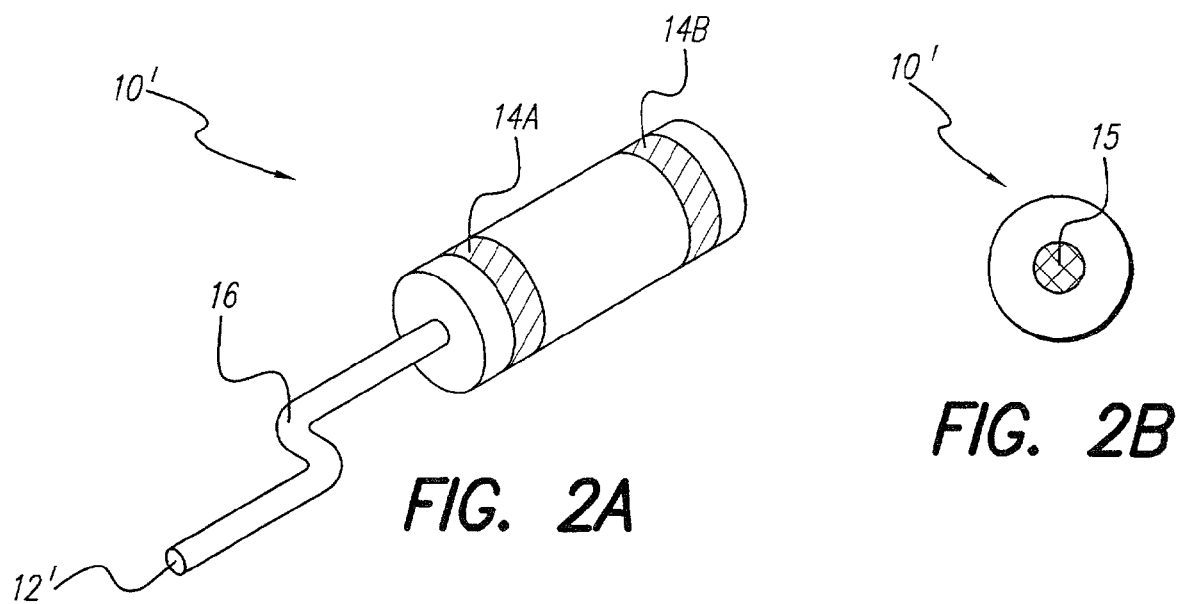
FIG. 2A
FIG. 2B
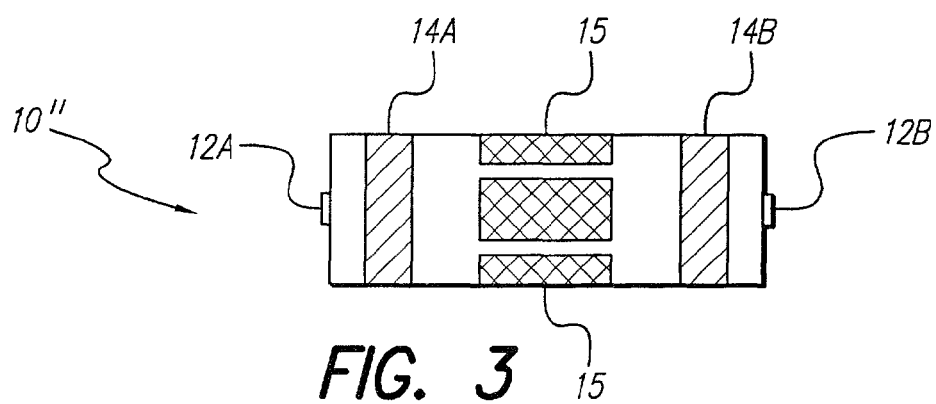
FIG. 3

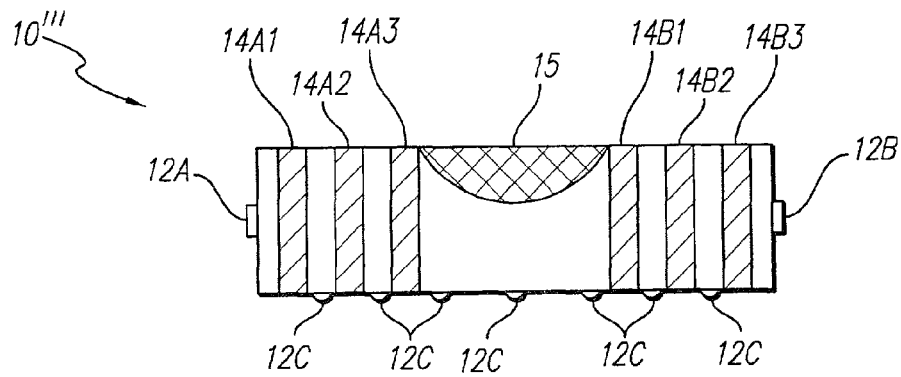
FIG. 4
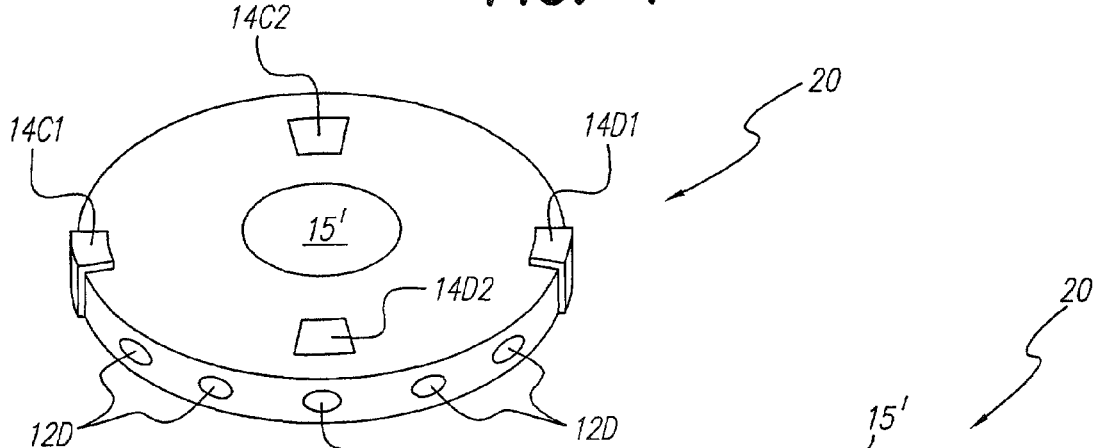
FIG. 5A
FIG. 5B
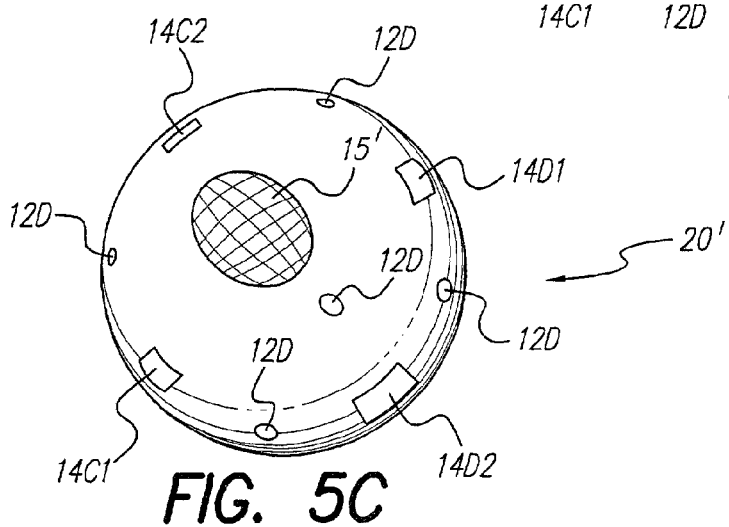
FIG. 5C

MICROMINIATURE INFUSION PUMP

The present application claims the benefit of U.S. Provisional Patent Application Ser. No. 60/265,419, filed Jan. 20, 2001, which application is incorporated herein by reference in its entirety.

FIELD OF THE INVENTION

The present invention generally relates to implantable medical devices, and more particularly to an implantable microminiature infusion pump; and/or a system comprising a plurality of implantable microdevices and external devices used to provide therapeutic substances, including electrical stimulation, to a patient.

BACKGROUND OF THE INVENTION

Pharmaceutical developments have yielded dozens of new drugs each year for the past decade. As the identification and understanding of the various hormones, cytokines, neurotransmitters, and various other chemical regulators and messengers has increased, the ability to harness these substances therapeutically also increases. Additionally, with the advent of gene therapy, a new method of treating disease is beginning to be developed.

The significant advances in the therapeutic substances delivered to patients have been accompanied by a somewhat slower development of methods and means of drug delivery. Some of the newer substances are simply not amenable to the paradigm of taking a pill once or a few times a day. For instance, a number of newly developed substances, such as peptides and strands of DNA, are deactivated or destroyed by the gastrointestinal system, immune system, liver, and/or lymphatic system before they reach the systemic circulation in any significant or reproducible level. Other substances must be maintained at a minimum level in order to achieve a therapeutic effect, e.g., heparin. Other substances have a narrow therapeutic window, i.e., the minimum required dose is not far below the maximum recommended dose. Additional examples exist, including substances that may need to be targeted to a site to avoid systemic side effects.

Several methods of convenient parenteral drug administration are now commercially available. Depot formulations of medications have been available for some years, e.g., Depo-Provera, a form of contraception that lasts to 3 months. Transdermal patches are available for the delivery of substances such as fentanyl, nicotine and testosterone. A long-lasting, slow-dissolving formulation of contraceptive is now available from Norplant, and provides a means of contraception that offers protection from pregnancy for up to 5 years.

More invasive systems have become available recently as well. External infusion pumps have been available for a number of years, e.g., the Medtronic MiniMed external insulin pump, made by Medtronic MiniMed Inc. of Northridge, Calif. Implantable infusion pumps are also available for systemic delivery of substances, e.g., the Medtronic MiniMed implantable insulin pump. External and internal infusion pumps are now also used for the delivery of substances to a targeted area, e.g., intrathecal delivery of opiates and cancer site delivery of chemotherapy agents. The infusion rate of some such systems may be adjusted transcutaneously.

The DURECT DUROS osmotic infusion pump, commercially available from Durect, of Cupertino, Calif., is typically implanted via a minimally invasive procedure and provides delivery of medication for up to several months. However, the infusion rate is not adjustable following implantation.

The following U.S. patents describe various types of infusion pumps known in the art: U.S. Pat. Nos. 3,731,681; 4,457,752; 4,557,673; 4,911,616; 5,041,107; 5,045,064; 5,049,141; 5,514,103; 5,637,095; 5,678,296; 5,697,951; 5,733,259; 5,785,681; 5,697,951; 5,733,259; 5,785,681; 5,820,589; 5,888,530; 5,957,890; 6,120,665; 5,667,491; 6,022,316; 6,014,584; 5,869,326; and 6,110,161.

SUMMARY OF THE INVENTION

A review of the above-referenced prior art indicates that there is still a need for a minimally-invasive implantable infusion pump that, once implanted, can be controlled in meaningful ways to customize it to suit the needs of a particular patient. Moreover, a review of the prior art indicates that there is also a need a minimally-invasive infusion pump that may be combined with other forms of treatment and therapy, e.g., electrical stimulation therapy.

The present invention provides means of subacute or chronic drug delivery via a microminiature infusion pump that can be implanted with a minimal surgical procedure. In some embodiments, the infusion rate may be programmed so that it may vary over time, or in response to an external stimulus, e.g., a command from a remote control. The micropump also, in some embodiments, incorporates means of electrical stimulation, thereby providing a complementary or additional therapy. For example, the pump combined with electrical stimulation may be used in the case of electrical nerve stimulation combined with analgesic infusion for pain control.

BRIEF DESCRIPTION OF THE DRAWINGS

The above and other aspects of the present invention will be more apparent from the following more particular description thereof, presented in conjunction with the following drawings wherein:

FIG. 1 is a perspective view of a microminiature infusion pump made in accordance with one embodiment of the invention. This drawing and accompanying text include, without limitation, various means or portions of means for delivering at least one therapeutic substance and/or therapeutic electrical stimulation to a patient.

FIG. 2A is a perspective view of an alternative embodiment of a microminiature infusion pump. This drawing and accompanying text include, without limitation, various means or portions of means for delivering at least one therapeutic substance and/or therapeutic electrical stimulation to a patient.

FIG. 2B is a view of one end of the infusion pump of FIG. 2A. This drawing and accompanying text include, without limitation, various means or portions of means for delivering at least one therapeutic substance and/or therapeutic electrical stimulation to a patient.

FIG. 3 is a side view of another embodiment of a microminiature infusion pump. This drawing and accompanying text include, without limitation, various means or portions of means for delivering at least one therapeutic substance and/or therapeutic electrical stimulation to a patient.

FIG. 4 is a side view of still another embodiment of a microminiature infusion pump. This drawing and accompanying text include, without limitation, various means or portions of means for delivering at least one therapeutic substance and/or therapeutic electrical stimulation to a patient.

FIG. 5A is a perspective view of a pancake-shaped embodiment of a microminiature device made in accordance with the invention. This drawing and accompanying text include, without limitation, various means or portions of means for delivering at least one therapeutic substance and/or therapeutic electrical stimulation to a patient.

FIG. 5B is a side view of the pancake-shaped embodiment of FIG. 5A. This drawing and accompanying text include, without limitation, various means or portions of means for delivering at least one therapeutic substance and/or therapeutic electrical stimulation to a patient.

FIG. 5C is a perspective view of a spherical embodiment of a microminiature device made in accordance with the invention. This drawing and accompanying text include, without limitation, various means or portions of means for delivering at least one therapeutic substance and/or therapeutic electrical stimulation to a patient.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

In the description that follows, reference should be made generally to the figures, FIGS. 1-8.

The present invention is directed to a system including means for delivering at least one therapeutic substance to a patient, the therapeutic substance delivery means comprising a microminiature implantable infusion pump, such as the pump 10 shown in FIG. 1, or the infusion pumps 10', 10", 10''', 20, or 20' shown in FIGS. 2 through 6. Such pump(s) may be filled with a fluid 39 (FIG. 6) that consists of and/or contains a therapeutic substance(s) to be delivered to a patient. In some embodiments of this invention, such as implantable infusion pump 10" (FIG. 3), the pump is capable of supplying direct current (DC) or electric current pulses with means for delivering therapeutic electrical stimulation to the patient, wherein the electrical stimulation means includes no less than two electrodes 14A and 14B and possesses one or more of the following properties:

(1) leadless;
(2) injectable (e.g., via a hypodermic needle or cannula); and
(3) implantable via endoscopy or laparoscopy.

Figure 6:
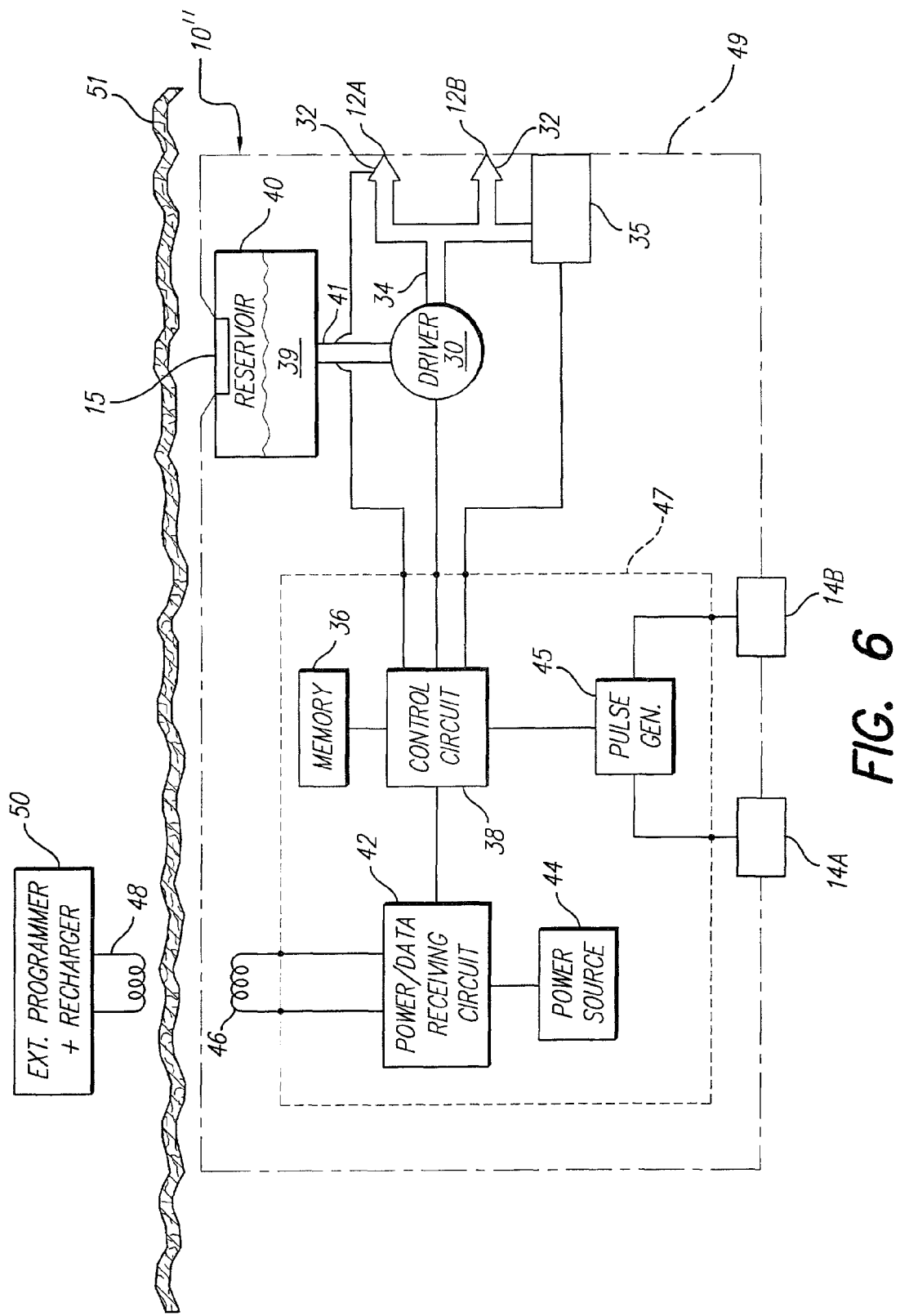
FIG. 6 is a functional block diagram of a microminiature device made in accordance with the invention that includes both infusion and electrical stimulation capabilities. This drawing and accompanying text include, without limitation, various means or portions of means for delivering at least one therapeutic substance and/or therapeutic electrical stimulation to a patient and for providing power to these delivery means.

As seen best in FIG. 6, the pump 10" includes a reservoir(s) 40 that contains a fluid(s) 39 that consists of and/or contains a therapeutic substance(s) to be delivered to a patient. Reservoir 40 is typically impermeable to the substance(s) that it contains. The reservoir may be relatively stiff or it may be flexible, e.g., a flexible bag-type reservoir or a deformable bellows.

The device also includes a driver 30 for driving a fluid(s) out an exit portal(s) 12A, 12B in the device. The driver 30 may be adjusted by circuitry 38 internal to the device, e.g., based on a desired time-infusion rate profile, and/or by an external device 50, e.g., a sensor device or a remote control. In some embodiments, the driver 30 is a pump of the diaphragmatic or peristaltic type, or the like, in which the moving part(s) force fluid out of the reservoir by creating areas of increased and/or decreased pressure and/or by applying force to the reservoir 40 or other temporary container of fluid(s). The driver 30, e.g., pump, may be actuated by electrostatic and/or electromagnetic means.

In certain embodiments, the driver 30 used to drive a fluid (s) out an exit portal(s) is a negative pressure pump (typified by U.S. Pat. Nos. 4,482,346 and 4,486,190, incorporated herein by reference). Such negative pressure pump may be a solenoid-activated negative pressure device. A diaphragm separates the drug from propellant, such as Freon maintained at negative pressure, or the like. The solenoid is activated, driving an armature and a bellows pumping element. The displacement of the armature opens a check valve that draws drug from a reservoir(s) into a downstream pumping chamber. A restriction is used to prevent backflow in the outlet during this short period. When the pump chamber is full, the check valve closes and the solenoid is de-energized. A spring force is used to displace the bellows into the chamber thereby pumping the drug through a restrictor and into the patient. The bellows armature assembly comes to rest on the check valve to insure that no backflow occurs during the rest period. Such a system operates at negative pressure to ensure no forward, flow during this rest period, i.e., the drug chamber pressure is less than body pressure.

In various embodiments, the driver 30 for driving a fluid(s) out an exit portal(s) comprises a positive pressure pump used in combination with an accumulator pump (typified by U.S. Pat. Nos. 4,221,219; 4,299,220; and 4,445,224, incorporated herein by reference). Such driver may also incorporate redundant or fail-safe valves together with sensor/shutdown circuits to prevent accidental delivery of the fluid(s) contained in the reservoir.

The microminiature pump 10" shown in FIGS. 3 and 6, or the device 10, 10', 10''', 20, or 20' shown in FIGS. 1, 2A and 2B, 4, or 5A, 5B, and 5C, respectively, also includes, in some embodiments, a regulator 32 for regulating or restricting flow. The regulator 32 may be adjusted by circuitry 38 internal to the device, e.g., based on a desired time-infusion rate profile, and/or by an external device 50, e.g., a sensor device or a remote control. In certain embodiments, the regulator 32 comprises a capillary tube(s). In various embodiments, the regulator 32 comprises a mechanical valves(s) that adjusts the size of a lumen of an exit portal or a catheter. Such mechanical valve(s) is/are typically actuated by mechanical, electrostatic, and/or electromagnetic means.

In several embodiments, the regulator 32 for adjusting infusion rate consists of a number of multi-stable valves. Such multi-stable valves may be of any suitable design apparent to those skilled in the art, e.g., shape-memory valves or micro-machined valves. The number of possible settings of the multi-stable valves determines the maximum possible number of allowable programmable states, i.e., infusion rates. In some embodiments, the regulator 32 alternatively or additionally includes a pressure responsive control valve for connecting a secondary restrictor such as an additional capillary tube in series with the baseline flow path, to prevent undesired increase in the infusion rate in the event that the patient temporarily encounters a high altitude ambient pressure.

The microminiature pump 10' of the invention also includes at least one an exit portal, allowing the fluid 39 to egress from the device. In some embodiments, an exit portal (s) 12A, 12B is/are substantially flush with the device, i.e., the device contains no catheter. The exit portals 12A and 12B are in fluid communication with the driver 30, e.g., pump, via tubing or channels 34, or the like. In various embodiments such as shown in FIG. 2, fluid egress entails one or more catheters 16 having one or more exit portals 12', for instance, at a distal end. In certain embodiments, fluid egress occurs by passing the fluid through a membrane or a filter near or part of an exit portal(s) on the surface of the device and/or part of a catheter attached to the device.

The microminiature pump device further includes, in some embodiments, a non-occlusion device 35 for ensuring that an exit portal(s) is not occluded or that it may be cleared if occluded, e.g., by tissue or debris from a patient's body. Such non-occlusion device 35 typically includes a mechanical device, such as a wiper or a plunger, that periodically or episodically clears an occluded lumen. Such non-occlusion device may alternatively or additionally include an electrical pulse(s) or other electrical signal that may disintegrate an occlusion. Such device may alternatively or additionally compress or expand the exit portal(s), such that the occlusion is broken down or is otherwise allowed to escape. Such non-occlusion device may alternatively or additionally include the application of a high fluid pressure behind the occlusion to force it out of the exit portal(s). Alternatively or additionally, the non-occlusion device may include a filter over the exit portal(s). The microminiature pump device may trigger the non-occlusion device upon sensing that an occlusion is present, e.g., through detection of increased pressure in the pump or the restrictor.

The microminiature pump device 10, 10', 10'', 10''', 20, or 20' of the present invention further includes, in certain embodiments, a means of transcutaneous refilling 15. For instance, one or more thin membranes 15 or septum-like material overlying one or more reservoirs 40 may be punctured by a hypodermic needle (e.g., syringe), but typically does not allow any significant leakage of fluid or substance following such puncture. For the embodiment shown in FIG. 1, membrane 15 covers a rectangular-shaped window formed in the side wall of the device 10, whereas in the embodiment shown in FIG. 4, membrane 15 covers a round-shaped window formed in the side wall of the device 10'''. For the embodiment shown in FIG. 2A, membrane 15 is formed in one end of the device 10', as shown in FIG. 2B. For the embodiment shown in FIG. 3, several membrane windows 15 are located around the side of the device 10''. For the embodiment shown in FIGS. 5A and 5B, a round-shaped membrane window 15 is located near the center of device 20. As depicted in FIG. 5C, one or more rounded septa 15 may be positioned as desired on a substantially spherical device 20'. As can be seen, one or more refilling means 15 may be used, and may be square/rectangular, rounded, at the end of the device, around the circumference of the device, or in any other useful shape or location. Additionally or alternatively, the microminiature pump contains a valve or other portal that is actuated by circuitry internal to the device and/or by an external device, e.g., an incoming syringe or a remote control. In such embodiments, this portal normally covers the reservoir but is retracted to expose the reservoir during a period of refilling.

Figure 7:
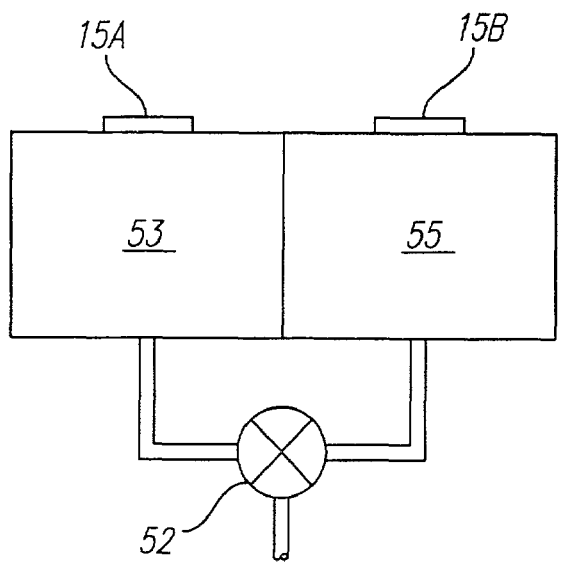
FIG. 7 schematically depicts an alternative configuration of the reservoir used within the device of FIG. 6. This drawing and accompanying text include, without limitation, various means or portions of means for delivering at least one therapeutic substance to a patient.

In embodiments as shown in FIG. 7, the microminiature pump device 10'' may further include a fluid mixer 52 for mixing fluids that are contained within multiple isolated reservoirs 53, 55 prior to delivery to the patient. Means of refilling 15A and 15B allow access to reservoirs 53 and 55, respectively. While only two isolated reservoirs 53 and 55 are shown in FIG. 7, such is only exemplary, and any number of isolated reservoirs could be used. Such mixer 52 allows, for instance, the delivery of substances that are otherwise too volatile to be stored within the patient for days or months. Such mixer 52 may also provide an additional safety mechanism in that an inert substance may be delivered should the device suffer a breach of a single reservoir.

The microminiature pump device 10'' additionally includes electrical stimulation means 45 for providing electrical stimulation of tissue, including two or more electrodes 14A and 14B that are on the surface of the device 10'' and/or on leads attached to the device. Such electrical stimulation may take the form of a series or sequence of electrical pulses of a type typically used for, e.g., stimulation of nerve and muscle tissue. Alternatively, such electrical stimulation may take the form of very high-voltage electrical pulses. The electrical stimulation may alternatively comprise an electrical generator that generates a DC or slowly varying waveform. The electrical stimulation means may be configured to operate in conjunction with the fluid infusion means of the microminiature pump device. Alternatively, the electrical stimulation means may operate as an alternative to the fluid infusion means. In the latter case, two microstimulators may be implanted: a microminiature drug delivery infusion pump and an electric stimulation "micro-pump".

Figure 8:
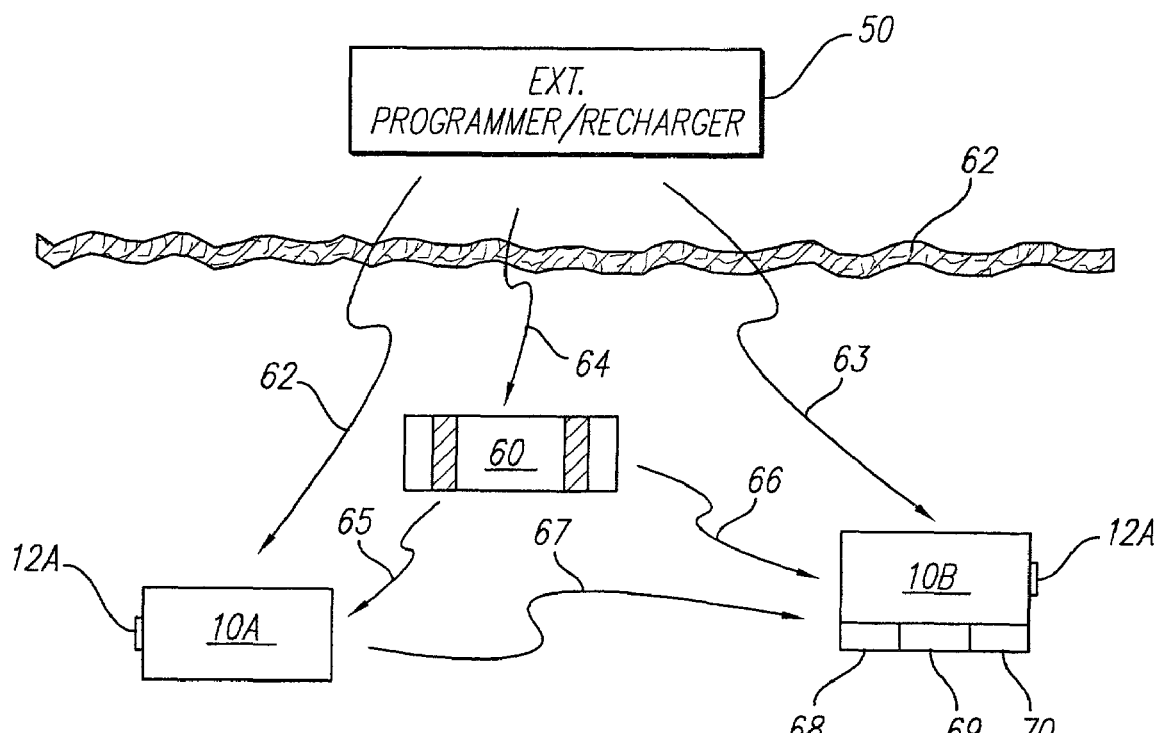
FIG. 8 depicts a system of implantable microdevices that communicate with each other and/or with external control/programming devices. This drawing and accompanying text include, without limitation, various means or portions of means for delivering at least one therapeutic substance and/or therapeutic electrical stimulation to a patient.

The microminiature infusion pump device of the invention may deliver one or more medications or other substances. A single device may be implanted, or two or more devices may be implanted to achieve drug infusion, pulses of electric current, and/or direct electric current application to a larger region or for a longer period of time, as shown in FIG. 8. In FIG. 8, a first infusion device 10A, implanted beneath the skin 51 of the patient, provides a first medication or substance; a second implanted infusion device 10B provides a second medication or substance; and a third implantable device 60 provides electrical stimulation. A somewhat more complicated surgical procedure may be required for purposes of fixing the device(s) in place.

Referring to FIG. 6, the device of certain embodiments of the invention includes a programmable memory 36 for storing set(s) of infusion parameters, electrical stimulation parameters, control parameters, and/or other data, if required. This allows, when needed or desired, infusion parameters, electrical stimulation parameters, and control parameters to be adjusted to settings that are safe and efficacious with minimal discomfort for each individual. Different parameters may have different effects on different patients, different diseases, and even different tissue.

The dotted line 47 shown in FIG. 6 represents the boundaries of an exemplary hermetically-sealed case in which a control circuit 38, memory 36, pulse generator circuitry 45, power/data receiving circuit 42, and power source/storage 44 are housed. The large heavy dots on line 47 represent electrical feed-through connectors that allow electrical access into hermetically-sealed case 47. The dashed-dotted line 49 represents the boundaries of the entire microdevice 10'', which contains other elements which may not necessarily be included within the hermetically-sealed portion 47. These elements include, e.g., an inductive coil 46 or the like for receiving and transmitting RF data and/or power (for instance, with inductive coils 48 or by other means of communication, such as an RF transmitter and receiver), a pump or other driver 30, a reservoir 40 for holding fluid 39 (e.g., a drug), tubing 41 connecting reservoir 40 with driver 30, tubing 34 connecting driver 30 with regulator 32 and/or non-occluding device 35, which non-occluding device 35 keeps the tubing 34 and regulator 32 free from occlusions. Depending upon the type of driver 30 used, portions thereof (e.g., electronic control circuits and/or elements) may also be included within the hermetically-sealed portion 47 of the device 10".

The length and the shape of the microminiature infusion pump may be varied in order to deliver more effective treatment. According to embodiments of the invention as shown in FIG. 1, a microminiature infusion pump 10 may comprise a thin cylindrical device with an exit portal 12 at one end. According to embodiments of the invention as shown in FIG. 3, a microminiature infusion pump 10" may comprise a thin cylindrical device with an exit portal 12A and 12B at both ends. According to embodiments of the invention as shown in FIG. 4, a microminiature infusion pump device 10''' may comprise a thin cylindrical device with an exit portal 12A and/or 12B at either or both ends and having additional exit portals 12C distributed along its body. According to various embodiments of the invention, the device is a thin cylindrical device with electrodes 14A, 14B at each end and with exit portals 12A, 12B, 12C at either or both ends and/or distributed along its body. According to embodiments of the invention as shown in FIGS. 5A, 5B, and 5C, the infusion device may be a relatively flat circular (i.e., pancake-shaped or disk-shaped) device (FIGS. 5A and 5B) or a substantially spherical device (FIG. 5C) with exit portals 12D and/or electrodes 14C, 14D, distributed around its periphery. The diameter/thickness of such device(s) may be varied depending upon the application for which it is used. For instance, disk-shaped device 20 may be, but is not necessarily, thicker in its center than at is edges, as shown in the side view of FIG. 5B. A septum 15', or other membrane, may be located on the surface of device 20 and/or 20' to allow a fluid to be injected into an internal reservoir.

The number and orientation of electrodes 14A, 14B, and/or 14C, 14D, that are present on a device made in accordance with the invention may be varied. According to embodiments of the invention as depicted in FIG. 3, a thin cylindrical microdevice may have an anode 14A at one end and a cathode 14B at the other. According to embodiments of the invention as shown in FIG. 4, a thin cylindrical microdevice may have a plurality of anodes 14A1, 14A2, 14A3 and/or cathodes 14B1, 14B2, 14B3 distributed along its surface. Certain embodiments provide a flat circular (i.e., pancake-shaped) stimulator device 20 as shown in FIGS. 5A and 5B, or a substantially spherical device 20' as shown in FIG. 5C, but having a plurality of anodes 14C1, 14C2 and/or cathodes 14D1, 14D2 distributed along their surface and periphery.

The microdevice of the present invention may be controlled to provide drug infusion and/or electric stimulation either intermittently or continuously. Specific infusion parameters and/or specific electrical parameters provide therapeutic advantages for various diseases. According to some embodiments of the invention, the infused substance(s) are administered systemically, and at the same time the microstimulator is activated to produce electric stimulation for a first period of time. The microstimulator continues to provide electric stimulation for a second predetermined period of time following the administration of the infused substance(s), e.g., two (2) hours. According to certain embodiments of the invention, the microstimulator provides electric stimulation continuously, and the electric stimulation may potentiate the effects of a substance(s) and/or may provide direct effects on tissue.

The power source used as a means for providing power to the implantable microdevice of the present invention may be realized using one or more of the following approaches, or other power source/storage options:

(1) an external power source coupled to the microdevice, e.g., via a radio-frequency (RF) link;

(2) a self-contained power source using any suitable means of generation and/or storage of energy, e.g., a primary battery, a replenishable or rechargeable battery, a capacitor, a super- or ultra-capacitor; and/or (3) if the self-contained power source is replenishable or rechargeable, means of replenishing or recharging the power source, e.g., an RF link, an optical link, a thermal link, or other energy-coupling link.

According to some embodiments of the invention, the implanted microdevice may operate independently. According to other embodiments of the invention, the implanted microdevice operates in a coordinated manner with other similar implanted microdevices, other implanted devices, or other devices external to the patient's body, e.g., as shown by the control lines 62, 63 and 64 in FIG. 8. For example, in accordance with certain embodiments of the invention, the external controller 50 controls the operation of each of the implanted devices 60, 10A and 10B. According to various embodiments of the invention, an implanted device, e.g., device 10A may control or operate under the control of another implanted device(s), e.g., micropump(s) 10B, another implanted device(s) 60, or another device(s) 50 external to the patient's body. That is, a device made in accordance with the invention may communicate with other implanted microminiature pumps, other implanted devices, and/or devices external to a patient's body, e.g., via an RF link, an ultrasonic link, or an optical link. Specifically, as illustrated in FIG. 8, a device 10A, 10B and/or 60, made in accordance with the invention, may communicate with an external remote control (e.g., patient and/or physician programmer 50) that is capable of sending commands and/or data to implanted device(s) and that is capable of receiving commands and data (e.g., sensed information) from implanted device(s).

A micro-pump device made in accordance with the invention may incorporate communication means for communicating with one or more external or site-specific drug delivery devices; and further may have the control flexibility to synchronize and control the duration of drug delivery. The associated drug delivery device typically, but not necessarily, provides a feedback signal that lets the control device know it has received and understood the command. The communication signal between the micro-pump device and the drug delivery device may be encoded to prevent the accidental or inadvertent delivery of drugs by other signals.

A micro-pump device made in accordance with the invention further incorporates, in some embodiments, a first sensor 68 for sensing therapeutic effects, clinical variables, or other indicators of the state of the patient. The micro-pump device may additionally or alternatively incorporate a second sensor 69 for sensing levels and or changes in one or more hormones, enzymes, neurotransmitters and/or their associated breakdown products, cytokines, medications and/or other drugs, and/or other substances in the blood plasma or local interstitial fluid, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). The micro-pump device may additionally or alternatively incorporate a third sensor 70 for sensing electrical current levels and waveforms supplied by another source of electrical energy. Sensed information may then be used to control the infusion and/or electrical parameters of the micro-pump device in a closed loop manner, as shown by control lines 66, 67, and 65, and/or by an external device(s), as shown by control lines 62, 63, and 64.

According to some embodiments of the invention, the sensing and infusion are both incorporated into a single micro-pump device. According to other embodiments of the invention, the sensing and electrical stimulation are both incorporated into a single micro-pump device. According to yet other embodiments of the invention, the sensing, drug infusion, and electrical stimulation are all incorporated into a single micro-pump device. According to various embodiments of the invention, the sensor(s) are incorporated into at least one "micro-pump device" (that may or may be capable of infusion), and the sensed information is, if desired, communicated to at least one other micro-pump device capable of infusion. The implant circuitry amplifies and transmits these sensed signals, if necessary, which may be analog or digital. Information sensed by the sensor(s) may then be used to control the electrical, infusion, and/or control parameters in a closed-loop manner.

Additionally, a sensor(s) described earlier may be used to orchestrate first the activation of one microdevice, and then, when appropriate, another microdevice targeting the same or another area of the body, in order to, for instance, control symptoms by a different means. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. An implantable microminiature system comprising:
    means for delivering at least one therapeutic substance to a patient, wherein the therapeutic substance delivering means is implanted in a patient;
    means for delivering therapeutic electrical stimulation to the patient, wherein the electrical stimulation means is integral with the therapeutic substance delivering means and is implanted in the patient;
    at least one sensor, wherein the sensor senses a need for a therapeutic effect of the at least one therapeutic substance and the electrical stimulation; and
    means for providing power to the therapeutic substance delivering means, the electrical stimulation delivering means, and the at least one sensor, wherein the power providing means is within the implantable microminiature system.

2. The implantable microminiature system of claim 1 further including at least one lead attached to the implantable microminiature infusion pump and wherein at least a portion of the means for delivering therapeutic electrical stimulation are carried by the at least one lead.

3. The implantable microminiature system of claim 1 wherein at least a portion of the means for delivering at least one therapeutic substance and at least a portion of the means for delivering therapeutic electrical stimulation are housed within a pancake-shaped housing.

4. The implantable microminiature system of claim 3 wherein at least a portion of the means for delivering at least one therapeutic substance is located on a circumferential edge of said housing.

5. The implantable microminiature system of claim 3 wherein a plurality of portions of the means for delivering at least one therapeutic substance are spaced apart along a circumferential edge of said housing.

* * * * *